United States Patent [19]

Sumiyoshi et al.

[11] Patent Number: 5,736,148
[45] Date of Patent: Apr. 7, 1998

[54] INFECTIOUS JAPANESE ENCEPHALITIS VIRUS CDNA CLONES THAT PRODUCE HIGHLY ATTENUATED RECOMBINANT JAPANESE ENCEPHALITIS VIRUS, AND VACCINES THEREOF

[75] Inventors: Hideo Sumiyoshi, Branford, Conn.; Charles H. Hoke, Jr., Columbia, Md.

[73] Assignee: The United States of America as represented by the Secretary of the Army, Washington, D.C.

[21] Appl. No.: 438,702

[22] Filed: May 11, 1995

Related U.S. Application Data

[63] Continuation-in-part of Ser. No. 348,882, Nov. 28, 1994, abandoned, which is a continuation of Ser. No. 76,886, Jun. 15, 1993, abandoned.

[51] Int. Cl.$^6$ .............................. A61K 39/12; C12N 7/04
[52] U.S. Cl. ........................................ 424/218.1; 435/236
[58] Field of Search ........................... 435/236; 424/218.1

[56] References Cited

PUBLICATIONS

Kaluzová et al. "Reverted Virulence of attenuated tick--borne encephalitis virus mutant is not accompanied with the changes in deduced viral envelope protein amino acid sequence" Acta Virologica 38: 133–140, 1994.

Aihara et al., "Identification of Mutations That Occurred on the Genome of Japanese Encephalitis Virus During the Attenuation Process" Virus Genes 5: 95–109 (1991).

Bowie et al., "Deciphering the Message in Protein Sequences: Tolerance to Amino Acid Substitutions" Science 237: 1306–1310 (Mar. 16, 1990).

Davis et al., "Attenuating Mutations in the E2 Glycoprotein Gene of Venezuelan Equine Encephalitis Virus: Construction of Single and Multiple Mutants in a Full-Length cDNA Clone" Virology 183:20–31 (1991).

Eckels et al., "Japanese encephalitis virus live-attenuated vaccine, Chinese strain $SA_{14}$–14–2; adaptation to primary canine kidney cell cultures and preparation of a vaccine for human use" Vaccine 6: 513–518 (1988).

Kumar et al., "Amino acid variations at a single residue in an autoimmune peptide profoundly affect its.

Mason et al., "Japanese Encephalitis Virus–Vaccinia Recombinants Produce Particulte Forms of the Structural Membrane Proteins and Induce High Levels of Protection Against Lethal . . . " Virology 180: 294–305 (1991).

Nitayaphan et al., "Nucleotide Sequence of the Virulent SA–14 Strain of Japanese Encephalitis Virus and Its Attenuated Vaccine Derivative, SA–14–14–2" Virology 177: 541–552 (1990).

Schlesinger et al., "New Approaches to Flavivirus Vaccine Development" Biotechnology 20:280–307 (1992).

Sumiyoshi et al., "Infectious Japanese Encephalitis Virus RNA Can Be Synthesized from In Vitro–Ligated cDNA Templates" J. Virol. 66: 5425–5431 (Sep. 1992).

Sumiyoshi et al., "Characterization of a Highly Attenuated Japanese Encephalitis Virus Generated from Molecularly Cloned cDNA" J. Infect. Dis. 171: 1144–1151 (May 1995).

Vaughn et al., "The Epidemiology of Japanese Encephalitis: Prospects for Prevention" Epidem. Rev. 14:197–221 (1992).

Venugopal et al., "Towards a new generation of flavivirus vaccines" Vaccine 12:966–975 (1994).

*Primary Examiner*—Ponnathapura Achutamurthy
*Assistant Examiner*—Phuong T. Bui
*Attorney, Agent, or Firm*—Foley & Lardner

[57] ABSTRACT cDNA clones containing the entire genome of Japanese encephalitis virus (JEV) were used to produce infectious, recombinant JEV particles with diverse virulence properties. Certain viruses retained the immunogenicity of JEV, but lacked the ability to cause encephalitis. The mutation associated with this loss of neurovirulence was localized to a nucleotide substitution in the codon encoding the 138th amino acid of the envelop protein, resulting in a mutation of an acidic amino acid to a basic amino acid. Attenuated viruses containing this mutation form the basis of a greatly improved, molecularly defined vaccine for the prevention of Japanese encephalitis in humans.

9 Claims, 9 Drawing Sheets

INFECTIOUS JAPANESE ENCEPHALITIS VIRUS CDNA CLONES THAT PRODUCE HIGHLY ATTENUATED RECOMBINANT JAPANESE ENCEPHALITIS VIRUS, AND VACCINES THEREOF

CROSS-REFERENCE TO RELATED APPLICATIONS

This application is a continuation-in-part application of U.S. Ser. No. 08/348,882, filed Nov. 28, 1994, now abandoned, which is a continuation application of U.S. Ser. No. 08/076,886, filed Jun. 15, 1993, now abandoned.

BACKGROUND OF THE INVENTION

1. Field of the Invention

The present invention relates to recombinant, attenuated Japanese encephalitis viruses that contain a single amino acid mutation in the envelop protein. In particular, this invention is directed to isolated DNA molecules encoding the genomes of such mutant Japanese encephalitis viruses. This invention also is directed to methods for preparing mutant Japanese encephalitis viruses from cultured animal cells. Moreover, the present invention relates to pharmaceutical compositions for providing protection from virulent Japanese encephalitis viruses.

2. Background

Japanese encephalitis virus (JEV) is a mosquito-borne flavivirus that induces severe encephalitic and neurologic disease manifestations, and that is the cause of many cases of acute fatal encephalitis each year in Asia. Typically, the symptoms of JEV infection appear following an incubation period of four to twenty days. Patients may arrive at a hospital with evidence of severe central nervous system infection, including high fever, paralysis, and coma. There is no effective treatment. Hoke et al., *J. Infect. Dis.* 165: 631 (1992). Approximately one-third of hospitalized patients will die within ten days, and another one-third will recover with severe permanent neuropsychiatric deficits. Each year more than 10,000 JEV-induced deaths are officially reported, although the actual number is estimated to be much higher. See, for example, Burke et al., "Japanese encephalitis," in THE ARBOVIRUSES: EPIDEMIOLOGY AND ECOLOGY, Volume 3, (Monath TP, ed.), pages 63–92 (CRC Press 1988).

The JEV genome is a single-stranded RNA molecule of approximately 11 kb that encodes ten proteins including three structural proteins, the capsid protein, the membrane protein and the envelop protein, as well as seven nonstructural proteins, NS1, NS2A, NS2B, NS3, NS4A, NS4B, and NS5. Sumiyoshi et al., *Virology.* 161: 479 (1987). Genomes of the virulent JEV strains JaOArS982, Nakayama, Beijing and $SA_{14}$, as well as the attenuated strain $SA_{14}$-14-2, have been analyzed at the molecular level, revealing a similar structural organization. Id.; McAda et al., *Virology* 158: 348 (1987); Hashimoto et al., *Virus Genes* 1: 305 (1990); Nitayaphan et al., *Virology* 177: 541 (1990). Yet the relationship between particular JEV proteins to virulence and disease is still poorly understood.

At present, there are three types of JEV vaccines: (1) vaccines obtained from virus grown in mouse brain or tissue culture in which the virus is rendered noninfectious by formalin treatment, (2) vaccines comprising viruses that have become attenuated by serial passage in animals, and (3) vaccines comprising a vector, such as a recombinant vaccinia vector, that expresses flavivirus proteins. Despite the public health importance of JEV, however, the currently available vaccines are flawed for various reasons.

A formalin-inactivated, mouse-brain-derived JEV vaccine was devised during World War II, and the vaccine has been used in Japan for more than 20 years. Use of the vaccine has been associated with a decrease in both morbidity and mortality due to JEV in Japan. Hoke et al., *N. Engl. J. Med.* 319: 608 (1988). Improved living standards, however, may account for some decrease in incidence of JEV disease.

Problems associated with the inactivated vaccine stem from the fact that the virus must be produced in live mice, harvested from mice by a laborious procedure, purified, and killed with formalin treatment. Since the formalin-treated virus does not replicate in the recipient, large quantities of viral antigen and repeated doses of the vaccine are required for successful immunization. In addition, the effect of immunization with a killed vaccine is rarely as long lasting as immunity provided by a live vaccine. Finally, the need to eliminate murine antigens and the need for careful monitoring of the inactivation process increase the cost of producing the vaccine. Accordingly, the inactivated vaccine is expensive to produce, and it is not suitable for most developing countries in which JEV is a significant problem.

Substantial efforts have been expended to develop an attenuated live vaccine. These efforts have been motivated by the hope that serial passage of JEV in mice would result in a virus that was attenuated in humans, as well. The most promising vaccines, described below, are not ideal candidates because the viruses have been found to contain many mutations, and the effects of these alterations are unknown.

The live, attenuated JEV strain $SA_{14}$-14-2 was produced empirically by serial passage in cell culture and in laboratory animals. A comparison of the nucleotide sequence of the attenuated virus $SA_{14}$-14-2 and its parent virus ($SA_{14}$) has revealed that the attenuated virus has 57 nucleotide substitutions, resulting in 24 amino acid substitutions. Aihara et al., *Virus Genes* 5: 95 (1991). The genome of the parent virus itself, however, is very divergent from the genomes of other wild-type JEV's. This observation raises a question about whether any strain derived from the parent would be suitable to protect those who are exposed to a variety of JEV strains.

The $SA_{14}$-14-2 vaccine virus has been used in field trials in humans in China. Seroconversion (neutralizing antibody) rates in humans vary from 60 to 90%. Ao et al., *Chinese J. Microbiol. and Immunol.* 3: 245 (1981). However, multiple vaccine doses are required to induce seroconversion, and each dose must be high-titered (approximately $10^6$ PFU). In this way, the $SA_{14}$-14-2 vaccine is similar to the inactivated vaccine described above. Moreover, the occurrence of Japanese encephalitis has been reported in vaccinees despite immunization with two high-titered vaccine doses.

$SA_{14}$-14-2 has been further passaged in primary canine kidney cells (PCK). Eckels et al., *Vaccine.* 6: 513 (1988). The resulting virus, SA-14-14-2-PCK, was sequenced and its virulence markers were characterized in cell culture and in laboratory animals. Nitayaphan et al., *Virology.* 177: 541 (1990); Hase et al., *Arch. Virol.* 130: 131 (1993). In laboratory mice, immunization with SA14-14-2-PCK, using a variety of doses and dose schedules, induced a low rate of seroconversion as measured by the presence of serum neutralizing antibodies. Moreover, almost all immunized laboratory mice died after intracerebral challenge of the parent virus, regardless of the immunizing vaccine dose.

The SA14-14-2-PCK virus also was used for a vaccine trial in China during the 1980's. However, the trial ended in failure because the vaccinees failed to develop JEV antibodies. The cumulative results with the JEV $SA_{14}$-2 and the PCK derivative indicate that the attenuated viruses behave more like an inactivated vaccine than a live vaccine.

Several candidate JEV vaccines have been produced in which JEV proteins are presented to the host by a carrier or by recombinant vector. The most promising vaccine to date uses a recombinant virus derived from the vaccinia virus designated as NYVAC. Neutralizing antibody has been detected in laboratory mice that have been inoculated with vaccinia-JEV recombinant viruses encoding JEV envelop protein. Although the inoculated mice were protected against intraperitoneal challenge with virulent virus, the neutralizing antibody titers and seroconversion rates were lower than that observed following immunization with a killed vaccine. Moreover, protection against JEV was only partial. Yasuda et al., J. Virology. 64: 2788 (1990); Mason et al., Virology 180: 294 (1991); Jan et al., Am. J. of Trop. Med. & Hyg. 48: 412 (1993). Accordingly, multiple immunizations with the recombinant vector are required to protect laboratory mice from lethal challenge. Furthermore, immunization with a vector expressing only the JEV envelop protein cannot stimulate the humoral and cellular immune systems to respond to all of the JEV proteins that are actively expressed in JEV infected cells.

In summary, live, attenuated vaccines are often preferred over other forms of vaccines because the attenuated vaccines (1) induce longer-lasting immunity based on both humoral and cellular responses, (2) are less expensive to produce, and (3) usually require only a single immunizing dose. On the other hand, the danger of vaccine reversion to virulence is a constant problem with empirically-derived live, attenuated vaccines.

A need therefore exists for an attenuated JEV vaccine that does not replicate in the nervous system and that induces an immune response against a variety of JEV proteins. Moreover, the genome of the attenuated JEV should be completely characterized, so that the presence of molecular determinants of the attenuated phenotype can be identified and verified in final vaccine preparations.

SUMMARY OF THE INVENTION

Accordingly, it is an object of the present invention to provide attenuated Japanese encephalitis viruses suitable for stimulating an immune response against JEV in animals.

It is a further object of this invention to provide DNA molecules having known nucleotide sequences that encode such mutant viruses.

These and other objects are achieved, in accordance with one embodiment of the present invention by the provision of an isolated, mutant Japanese encephalitis virus (JEV) that is distinguished from the corresponding wild-type JEV by the replacement of an acidic amino acid for a basic amino acid at position 138 of the envelop protein, wherein the acidic amino acid is glutamic acid or aspartic acid, and wherein the basic amino acid is lysine or arginine.

In a preferred embodiment, the wild-type JEV is JEV strain JaOArS982, and the basic amino acid of the mutant JEV is lysine. In a more preferred embodiment, the wild-type JEV is JEV strain JaOArS982, and the basic amino acid of the mutant JEV is arginine.

The present invention also provides an isolated DNA molecule encoding the genome of a mutant JEV, wherein the mutant JEV is distinguished from the corresponding wild-type JEV by a mutation consisting of one or two nucleotide substitutions in the gene encoding the envelop protein. In particular, the present invention provides such DNA molecules wherein the mutation results in the replacement of an acidic amino acid at position 138 of the envelope protein of the wild-type JEV for a basic amino acid at position 138 in the envelope protein of the mutant JEV, wherein the acidic amino acid is glutamic acid or aspartic acid, and wherein the basic amino acid is lysine or arginine.

The present invention further provides a method for preparing mutant JEV from cultured animal cells, comprising:

(a) synthesizing full-length viral genomic RNA in vitro using a DNA molecule that encodes a mutant JEV as a template;

(b) transfecting cultured animal cells with the viral genomic RNA to produce virus; and (c) isolating the virus from the cultured animal cells.

The present invention also contemplates a method for producing neutralizing antibodies against JEV in an animal, comprising the administration of a therapeutically effective amount of a pharmaceutical composition comprising (a) a mutant JEV, and (b) a pharmaceutically acceptable vehicle, wherein the mutant JEV is distinguished from the corresponding wild-type JEV by the replacement of an acidic amino acid for a basic amino acid at position 138 of the envelop protein.

The present invention also provides pharmaceutical compositions comprising such mutant JEV and a pharmaceutically acceptable vehicle. Such pharmaceutical compositions may be administered to mucosa or administered by a form of injection selected from the group consisting of subcutaneous injection, intradermal injection and intramuscular injection.

The present invention further contemplates a method for producing mutant JEV, comprising:

(a) synthesizing full-length viral genomic RNA in vitro using a DNA template comprising the cDNA insert of pM343 (ATCC No. 75490);

(b) transfecting a monolayer culture of animal cells with the viral genomic RNA, wherein the transfection results in the formation of virus-containing plaques of various sizes within the monolayer culture; and (c) isolating virus from the smaller plaques within the monolayer culture.

The present invention also provides an isolated, mutant flavivirus that is distinguished from the corresponding wild-type flavivirus by the replacement of an acidic amino acid in the envelop protein of the wild-type flavivirus for a basic amino acid in the envelop protein of the mutant flavivirus, wherein the flavivirus is selected from the group consisting of Murray Valley encephalitis virus, St. Louis encephalitis virus, tick-borne encephalitis virus and Central European encephalitis virus, wherein the acidic amino acid is glutamic acid or aspartic acid, and wherein the basic amino acid is lysine or arginine.

DETAILED DESCRIPTION

1. Overview

As described above, there is a need for a safe, effective, and economical live JEV vaccine for human use. Previous attempts to develop a live attenuated vaccine utilized the empirical method of serial passages of wild-type viruses in murine hosts. In this approach, many mutations are introduced at random, and one can only hope that such mutations give rise to the attenuated phenotype.

To overcome these limitations, the inventors developed a system to produce JEV from infectious cDNA clones. Unexpectedly, this methodology produced highly attenuated viruses. The structure and function of these mutant viruses have been characterized, and additional attenuated viruses were produced using in vitro mutagenesis. The results of these studies have led to the discovery of a neurovirulence locus for JEV at amino acid position 138 in the envelope protein.

The methods described herein enable the production of greatly improved live attenuated vaccines for JEV. In addition, the elucidation of the neurovirulence locus may be used to generate vaccines against other neurovirulent flaviviruses.

2. Construction of Infectious JEV cDNA clones

Methods for constructing infectious JEV cDNA clones are described by Sumiyoshi et al., *J. Virol.* 66: 5425 (1992), which is incorporated by reference. Briefly, oligonucleotide primers were synthesized that represent the 3' and 5' ends of the genome of JEV strain JaOArS982 ("parent JEV"). The nucleotide sequence of the parent JEV is disclosed by Sumiyoshi et al., *Virology* 161: 497 (1987). First strand synthesis was accomplished using the 3'-end primer and parent JEV genomic RNA as the reverse transcriptase template. Double-stranded cDNA was synthesized using the 5'-end primer and the first strand of cDNA as the template. The cDNA molecules then were digested with BamHI and SalI, and the fragments were inserted into pBR322. A cDNA library was constructed by transforming competent *E. coli* HB101 cells with the recombinant pBR322.

Figure 2:
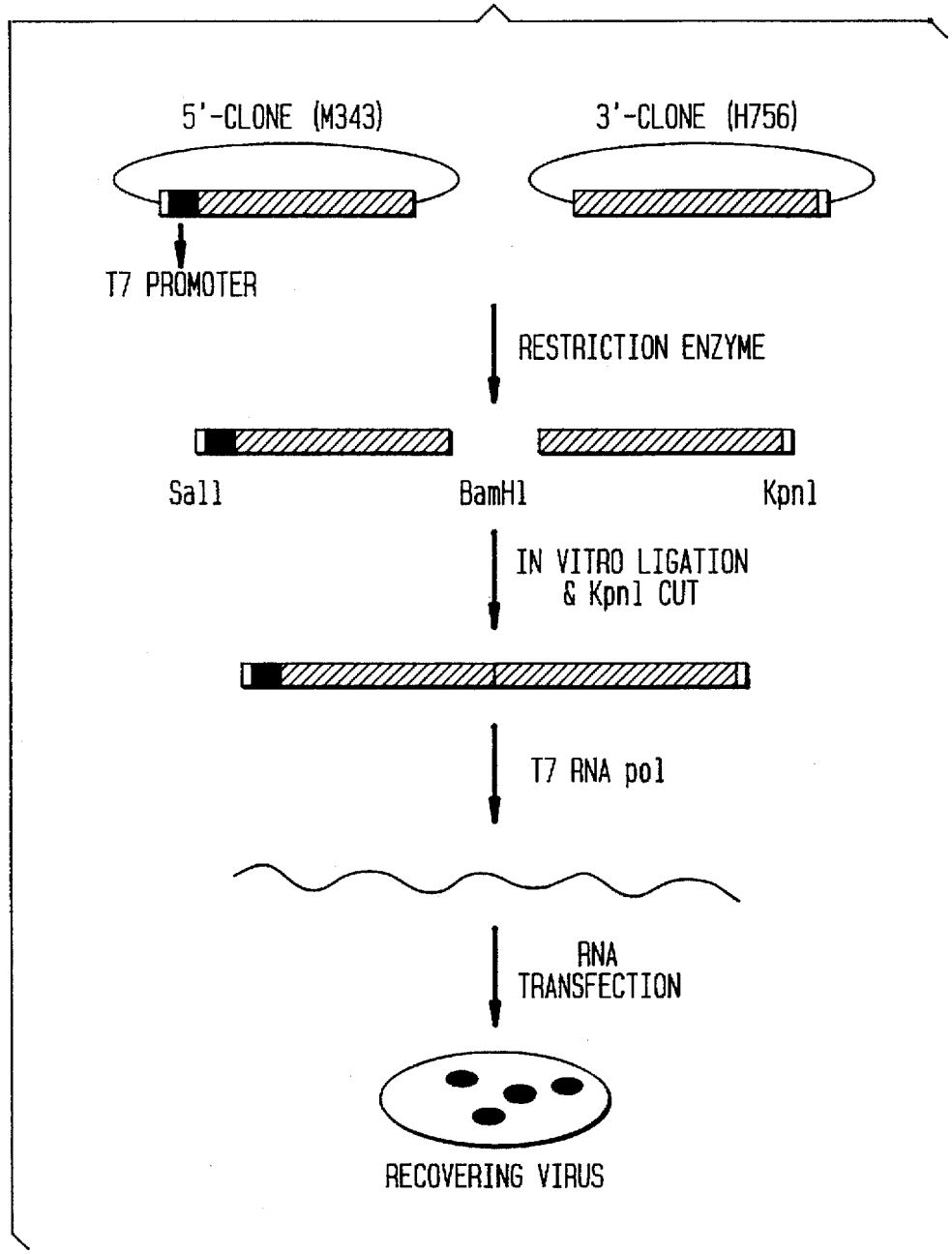
FIG. 2 presents the strategy for recovering recombinant wild-type JEV from cDNA. 5'-half JEV cDNA (pM343) and 3'-half cDNA (pH756) were purified from their respective cDNA clones and ligated in vitro to produce a full-length DNA template for T7 RNA polymerase. JEV RNA was transcribed from the cDNA templates, and the RNA was transfected into monolayer BHK-21 cells. Following a two-five day incubation, JEV plaques were visualized by staining with neutral red or crystal violet.

A full-length DNA copy of the JEV genome was constructed by in vitro ligation of two cDNA molecules, each encoding approximately half of the viral genome. As an illustration, the full-length JEV cDNA designated "IC37" was produced using the 5'-half cDNA clone pM343, which contains the JEV sequence from nucleotide 1 to nucleotide 5576. See FIG. 2. A cDNA molecule containing the 3'-half of the JEV genome was obtained by isolating a 5,400 base pair fragment from the cDNA clone, pH756; this fragment contains a portion of the JEV genome from nucleotide 5577 to the 3'-end. Finally, the 3'- and 5'-end clones were ligated to produce the full-length JEV cDNA clone, IC37.

Infectious JEV was obtained using IC37 as a template for RNA transcription, as described in Example 1 and by Sumiyoshi et al. (1992). Transcription products were transfected into cultured, mammalian cells, and infectious Japanese encephalitis viruses were recovered from the transfected cells. As described below, viruses produced from IC37 appear to be functionally identical to the parent JEV. Accordingly, infectious viruses obtained from the IC37 cDNA are referred to as the "recombinant wild-type JEV."

3. Construction of cDNA Molecules Encoding Mutant JEV

The above-described approach can be used to obtain Japanese encephalitis viruses having mutated genomes. The ultimate objective of in vitro mutagenesis is to produce efficacious attenuated vaccines. As a test case, one particularly useful mutation was introduced into the cDNA molecule designated pH756, which encodes the 3'-end of the JEV genome.

As described in Example 2, site-directed mutagenesis was used to introduce a silent mutation that removed a XbaI restriction site. The mutated cDNA, "pH756X," and pM343 were ligated together, and the ligated DNA was subjected to a T7 polymerase reaction to produce RNA transcripts. Cultured cells were transfected with RNA, and infectious JEV was recovered from the transfected cells. Viral genomic DNA molecules were prepared by reverse transcription-polymerase chain reaction. Subsequent sequence analysis revealed that the specific silent mutation was present in the genome of the recovered virus. These results proved that particular mutations could be introduced into the JEV genome using the methods described herein, and that the mutations are stable.

4. Preparation of Recombinant Attenuated JEV

Figure 1A:
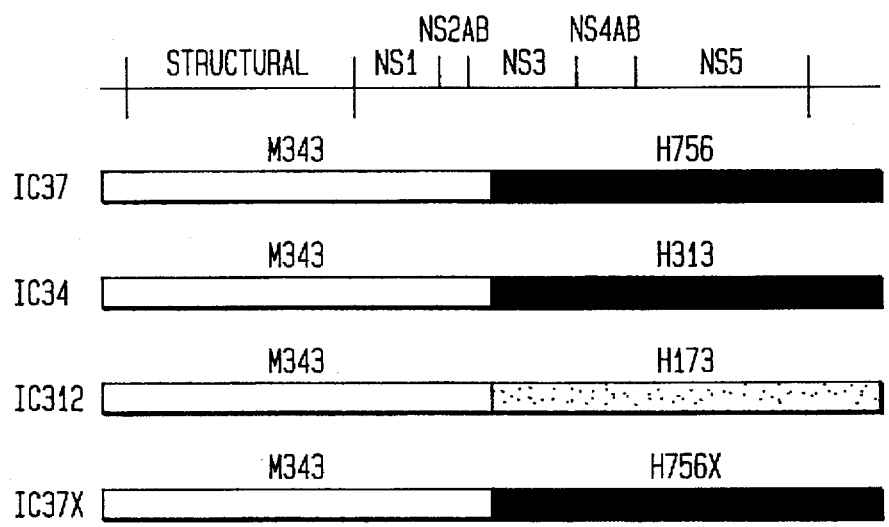
FIG. 1 presents a diagram of the JEV genome, as well as the structures of recombinant JEV viruses.
Figure 1B:

As illustrated in FIG. 1, various infectious JEV cDNA clones were constructed by ligating combinations of 5' and 3' cDNA clones. Specifically, 5' fragments from pM343 and pM433 were ligated with 3' fragments from pH756, pH313, pH173 and pH756X. The cDNA clones pM343, pM433 and pH756 were deposited with the American Type Culture Collection (ATCC; Rockville, Md.) on Jun. 17, 1993, and the plasmids were assigned ATCC Nos. 75490, 75491 and 75492, respectively. Japanese encephalitis virus JaoArS982 strain IC47 was deposited with the ATCC on Jun. 17, 1993, and was assigned ATCC No. VR 2412.

When cultured in hamster kidney cells, all recombinant viruses appeared to grow at similar rates. Viruses containing the 5' cDNA, pM433, however, produced plaques that were distinctly smaller than the plaques produced by the virulent parent JEV. Such small plaques may indicate that a virus is attenuated. As described herein, the inventors discovered that full-length JEV cDNA clones derived from pM433 were avirulent, whereas JEV cDNA clones derived from pM343 were virulent. See Examples 1, 2 and 4.

Nucleotide sequence analysis revealed that pM433 contains a single nucleotide substitution, compared with pM343. In the envelop protein of pM343, the 138th amino acid is glutamic acid encoded by GAA, while position 138 in the envelop protein of pM433 is lysine encoded by AAA. These results represent the first and only unambiguous definition of a locus for neurovirulence in the genome of neurotropic flaviviruses.

These studies also indicate that an additional attenuated JEV can be produced by mutating the wild-type codon GAA to AAG, which also encodes lysine. Mutations can be introduced into a cDNA molecule encoding the 5'-end of the JEV genome using well-known techniques, such as oligonucleotide-directed mutagenesis, linker-scanning mutagenesis, mutagenesis using the polymerase chain reaction, and the like. See Example 1, and Ausubel et al. (eds.), CURRENT PROTOCOLS IN MOLECULAR BIOLOGY, at pages 8.0.3–8.5.9 (John Wiley & Sons 1990). Also see generally, McPherson (ed.), DIRECTED MUTAGENESIS: A PRACTICAL APPROACH (IRL Press 1991).

More generally, the discovery of the neurovirulence locus indicates that an acidic amino acid at position 138 of the envelop protein is associated with virulence, while a basic amino acid at this position gives rise to the attenuated phenotype. Accordingly, one should be able to retain the virulent phenotype by mutating $^{138}$Glu to $^{138}$Asp. In contrast, one should be able to produce attenuated JEV by mutating the acidic amino acid at position 138 of the envelop protein to the basic amino acid arginine. Such attenuated mutants can be obtained by altering the wild-type codon GAA to CGT, CGC, CGA, CGG, AGA or AGG.

The studies presented in Example 7 confirm this hypothesis. Briefly, the inventors found that recombinant JEV containing $^{138}$Asp in the envelop protein was lethal in mice, whereas recombinant JEV having an AGA (Arg) codon at position 138 displayed the attenuated phenotype.

The discovery of the neurovirulence locus at position 138 of the envelop protein may be applied to produce attenuated vaccines for other neurovirulent flaviviruses, such as Murray Valley encephalitis virus, St. Louis encephalitis virus, tick-borne encephalitis virus, and Central European encephalitis virus. The viruses can be obtained from public depositories, such as the American Type Culture Collection (Murray Valley encephalitis virus: ATTC No. VR-77; St. Louis encephalitis virus: ATCC Nos. VR-80 and VR-1265).

Alternatively, DNA molecules encoding flavivirus genomes can be obtained by chemical synthesis using published nucleotide sequences. Such DNA molecules may be obtained, for example, by synthesizing the genes with mutually priming long oligonucleotides. See, for example, Ausubel at pages 8.2.8 to 8.2.13. Also, see Wosnick et al., *Gene* 60:115 (1987). Moreover, these techniques can be augmented by using the polymerase chain reaction to synthesize genes as large as 1.8 kilobases in length. Adang et al., *Plant Molec. Biol.* 21: 1131 (1993); Bambot et al., *PCR Methods and Applications* 2: 266 (1993). Mandl et al., *Virology* 194: 173 (1993), disclose the nucleotide sequence of tick-borne flavivirus Powassan, while the nucleotide sequence of Western subtype tick-borne encephalitis virus is disclosed by Mandl et al., *Virology* 166: 197 (1988), and by Mandl et al., *Virology* 173: 291 (1989).

In summary, it is possible to construct attenuated JEV by mutating the acidic amino acid residue at position 138 of the envelop protein to a basic amino acid residue. Example 7 shows that a nonvirulent JEV having a single nucleotide substitution retained the attenuated phenotype after ten passages through murine hosts. Nevertheless, preferred attenuated Japanese encephalitis viruses contain two nucleotide substitutions to ensure that reversion to wild-type is even less likely. Accordingly, preferred attenuated JEV contain an arginine residue at position 138 of the envelop protein, since two nucleotide substitutions are required to convert a codon encoding arginine to a codon encoding either glutamic acid or aspartic acid.

5. Use of Recombinant Attenuated JEV in Vaccines

As discussed above, mutant JEV strain $SA_{14}$-14-2 exhibits the attenuated phenotype in laboratory animals, such as mice, and inoculation of humans with the strain stimulates neutralizing antibody production. Also, see Eckels et al., *Vaccine* 6: 513 (1988). On the other hand, the SA14-14-2-PCK virus induces low rates of seroconversion in mice, and the virus fails to stimulate neutralizing antibodies in humans. Studies with attenuated JEV, therefore, show a correlation between the ability of an attenuated JEV strain to induce seroconversion in mice and in human vaccinees. Accordingly, the results of in vivo studies presented herein indicate that the mutant Japanese encephalitis viruses of the present invention should be particularly efficacious in stimulating an immune response in human vaccinees.

Since viruses are intracellular obligate parasites that cannot be grown on inanimate media, attenuated JEV must be propagated in animate media, such as cultured mammalian cells and chick embryo cell cultures. Techniques for purifying attenuated viruses from host cells are well-known to those of ordinary skill in the art. See, for example, Wang et al., *Chin. J. Virol.* 6: 38 (1990), who describe a method for preparing an $SA_{14}$-14-2 vaccine from infected tissue culture cells. Also see, generally, REMINGTON'S PHARMACEUTICAL SCIENCES, 18th Ed. (Mack Publishing Co. 1990).

Modes of administration of attenuated virus vaccines and suitable dosages of such vaccines are well known to those of skill in the art. See, for example, REMINGTON'S PHARMACEUTICAL SCIENCES, 18th Ed. (Mack Publishing Co. 1990). For example, attenuated JEV vaccine can be administered to a human recipient by intramuscular injection, by subcutaneous injection, or by intradermal injection. In general, the dosage of vaccine will vary depending upon such factors as the recipient's age, weight, height, sex, general medical condition and previous medical history. In general, 0.5–1 milliliter of vaccine will be administered as a formulation that contains $10^2$–$10^6$ PFU/milliliter. Experience with JEV attenuated vaccine, $SA_{14}$-14-2 provides general guidelines for suitable dosages of the recombinant attenuated JEV described herein. See, for example, Yu et al., *Chin. J. Microbiol. Immunol.* 1: 77 (1981), Ao et al., *Chin. J. Microbiol. Immunol.* 3: 245 (1983), Yu et al., *Am. J. Trop. Med. Hyg.* 39: 214 (1988), and Tsai et al., "Japanese Encephalitis Vaccines," in VACCINES, 2nd EDITION, Plotkin et al. (eds.), pages 671–713 (W.B. Saunders Co. 1994).

The vaccines of the present invention can be formulated according to known methods to prepare pharmaceutically useful compositions, whereby attenuated viruses are combined in a mixture with a pharmaceutically acceptable vehicle. A composition is said to be a "pharmaceutically acceptable vehicle" if its administration can be tolerated by the recipient. Sterile phosphate-buffered saline is one example of a pharmaceutically acceptable vehicle. Other suitable vehicles are well-known to those in the art. See, for example, REMINGTON'S PHARMACEUTICAL SCIENCES, 18th Ed. (Mack Publishing Co. 1990).

For purposes of therapy, attenuated JEV and a pharmaceutically acceptable vehicle are administered to a human recipient in a therapeutically effective amount. The combination of virus and a pharmaceutically acceptable vehicle is said to be administered in a "therapeutically effective amount" if the amount administered is physiologically significant. An agent is physiologically significant if its presence results in a detectable change in the physiology of the recipient. In the present context, an agent is physiologically significant if its presence stimulates the production of neutralizing antibodies against Japanese encephalitis virus.

The present invention, thus generally described, will be understood more readily by reference to the following examples, which are provided by way of illustration and are not intended to be limiting of the present invention.

EXAMPLE 1

Development of Infectious cDNA Clones Encoding Wild-Type JEV or Mutant JEV

A. Construction of JEV cDNA Clones

An infectious wild-type JEV cDNA clone encoding strain JaOArS982 was constructed as described by Sumiyoshi et al., *J. Virol.* 66: 5425 (1992), which is incorporated by reference. Briefly, two cDNA clones (pM343 or pM433) encoding the 5'-half of the JEV genome and a cDNA (pH756) corresponding to the 3'-half of the genome were ligated in vitro to produce two full-length templates for T7 RNA polymerase. See FIG. 2. A 50 µl RNA synthesis reaction mixture contained 1 µg of cDNA template, 40 mM Tris-HCl (pH 8.0), 25 mM NaCl, 8 mM $MgCl_2$, 2 mM spermidine, 5 mM dithiothreitol, 1 mM each CTP, UTP, and GTP, 0.1 mM ATP, 1 mM $m^7G(5')ppp(5')A$, 5 U of RNase inhibitor, and 0.2 µl of T7 RNA polymerase.

RNA molecules transcribed from the cDNA templates were transfected into BHK-21 cells, and progeny viruses were recovered. Chou et al., *Adv. Enzym. Relat. Areas Mol. Biol.* 47: 45 (1978). In these studies, BHK-21 cells were grown in minimal essential medium (MEM) supplemented with 10% fetal calf serum (FCS), 2 mM L-glutamine, 0.1 mM MEM nonessential amino acids, 0.3% sodium bicarbonate, 10 U/ml of penicillin, and 10 µg of streptomycin. Monolayers of BHK-21 cells in 35 mm dishes were washed with phosphate-buffered saline (PBS), and the cells were incubated with 400 µl of PBS containing RNA transcripts and 10% Lipofectin® (Bethesda Research Laboratories, Inc.; Gaithersburg, Md.) at room temperature for 10 minutes. The cells then were washed with PBS, and overlaid with 1% agarose that contained 2% FCS in MEM. After a two to three day incubation, cells were stained with neutral red to visualize virus plaques.

The virus recovered from the full-length cDNA derived from 5'-half pM343 and 3'-half pH756 was designated as IC37. This recombinant virus displayed properties that were indistinguishable from those of the parent JEV. The virus recovered from the cDNA template prepared from pM433 and pH756 was designated as IC47. Surprisingly, the characteristics of IC47 are distinct from those of the parent virus and IC37.

B. Site-Directed Mutagenesis of Wild-Type JEV Clones

The cDNA clone, pH756, contains a unique XbaI restriction site at nucleotide position 9131. Site directed in vitro mutagenesis was used to introduce a nucleotide substitution that removed the XbaI site without altering the amino acid sequence (i.e., a silent mutation). Studier et al., *J. Mol. Biol.* 189: 113 (1986). The mutated cDNA was used as a template for the T7RNA polymerase reaction, and virus was recovered using the procedures described above.

Genomic RNA was purified from the recovered virus particles, and the RNA was used as a template for cDNA synthesis and polymerase chain reaction (PCR) amplification. Restriction analysis of the resulting cDNA revealed that the clone lacked the XbaI site at nucleotide 9131. The results showed that (1) the recovered virus was derived from the altered cDNA and was not a contaminant, and (2) site-specific mutation can be introduced into a Japanese encephalitis virus by these techniques.

C. Structural and In Vitro Functional Analyses of JEV cDNA Clones

Figure 3:
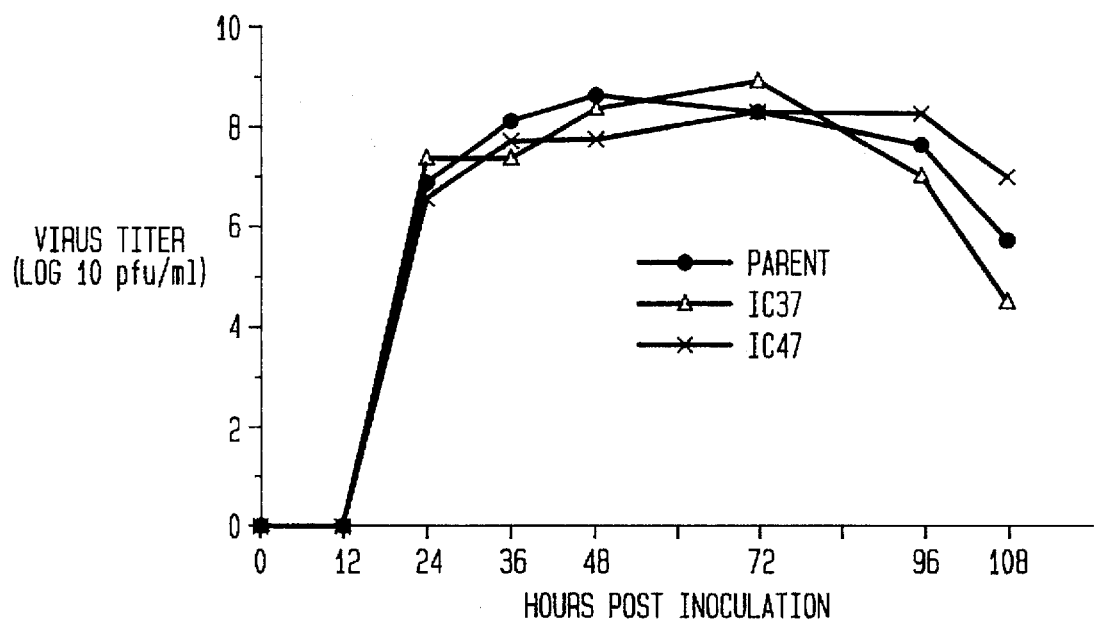
FIG. 3 shows the growth rates of parent JEV, recombinant wild-type (IC37) and recombinant mutant JEV (IC47) in BHK cells.

The growth rates of parent, IC37 and IC47 viruses were compared in BHK-21 cells infected at a multiplicity of 10 PFU per cell. See FIG. 3. Although the viruses could not be distinguished on the basis of growth rate, the plaque size of IC47 was much smaller than that of the parent and IC37.

Figure 4:
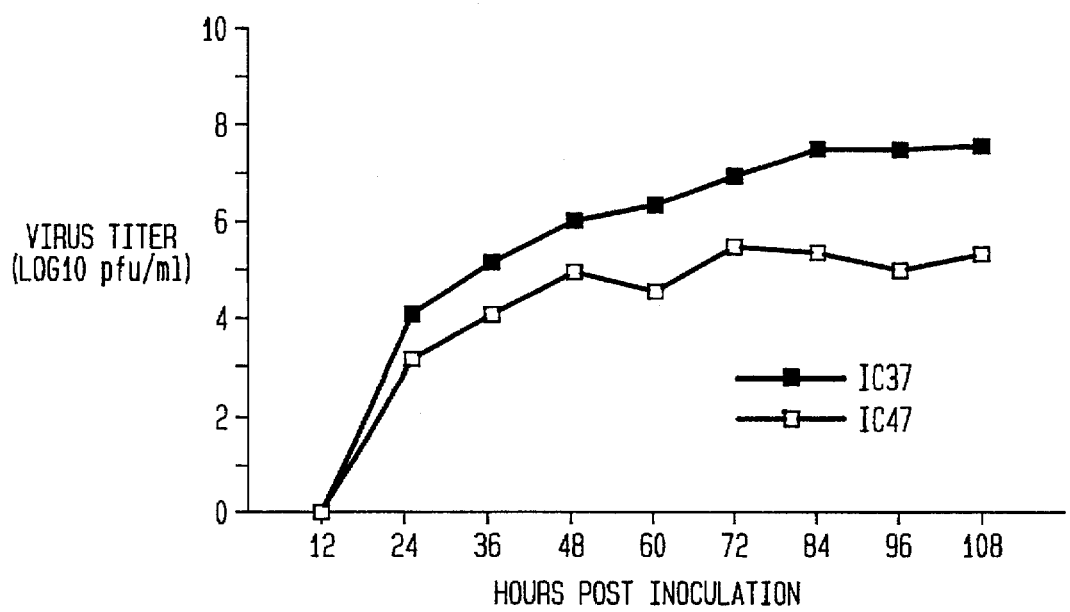
FIG. 4 shows the growth rates of recombinant wild-type (IC37) and recombinant mutant JEV (IC47) in N18 cells.

BHK-21 cells originally were isolated from kidney tissue. To examine the growth of IC37 and IC47 in cells derived from neuronal tissue, N18 cells were incubated with either virus at a multiplicity of 10 PFU per cell. As shown in FIG. 4, IC37 grew at a greater rate, compared with IC47. This observation may be relevant to the low rate of IC47 growth in murine brain tissue and to the attenuated phenotype of IC47, as described below.

Figure 5:
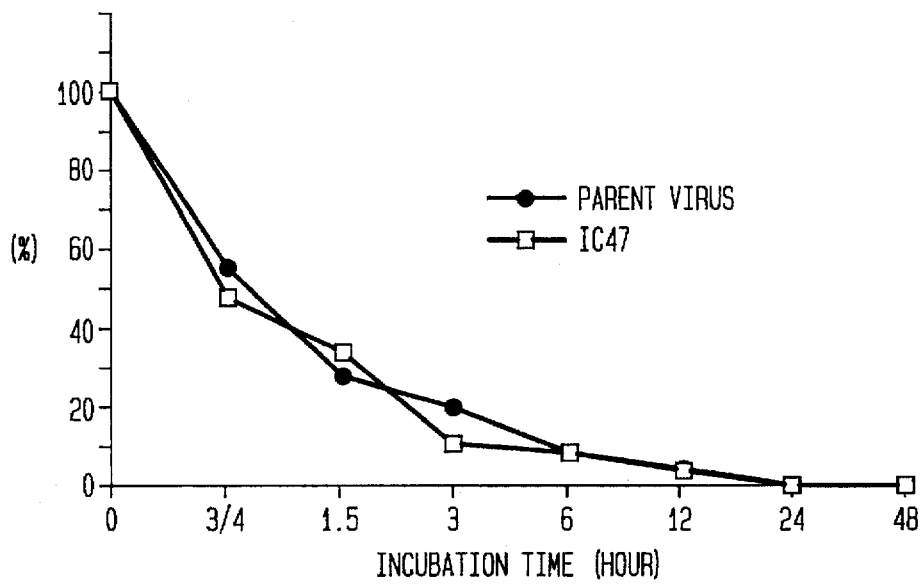
FIG. 5 shows the stability of parent JEV or mutant JEV (IC47) in culture medium.

To compare the stabilities of the parent and IC47 viruses, solutions of culture medium containing 10% FCS and 1000 PFU/ml of parent or IC47 were incubated at 37° C. in a $CO_2$ incubator. Virus was titrated at each time point by plaque assay. As shown in FIG. 5, there was no obvious difference in virus stability.

Nucleotide sequence analysis of cDNAs revealed that pM343 (i.e., the 5'-half of IC37) and pM433 (i.e., the 5'-half of IC47) differ by a single codon at position 138 in the envelop protein. In the envelop protein of pM343, the 138th amino acid is glutamic acid encoded by GAA, while position 138 in the envelop protein of pM433 is lysine encoded by AAA. Since the 3'-halves of IC37 and IC47 were derived from the same cDNA clone, these results indicate that a single amino acid change in the envelop protein at position 138 results in an altered plaque size. The mutation also results in a profound change in neurovirulence, as described below.

EXAMPLE 2

Neurovirulence of Wild-Type JEV, IC37 and IC47 Viruses in Mice

The recombinant viruses, IC37 and IC47, and the parent JEV were compared for neurovirulence using Swiss ICR mice. In preliminary experiments, three-week old mice were inoculated with 10 to $10^6$ PFU using either intracerebral (ic) or intraperitoneal (ip) administration. All of the mice that had been inoculated ic with the parent virus or with IC37 died, while the mortality of mice that had been inoculated ip with either virus was about 50%. In contrast, all of the mice that had been inoculated with IC47 either by the ic route or by the ip route survived the treatment. These studies showed that IC37 and the parent virus were indistinguishable in their ability to kill mice, while IC47 was not virulent.

In a second set of studies, groups of eight Swiss ICR outbred mice were challenged with parent virus, IC37, or IC47. Three- and five-week-old mice were used for ic inoculations of 100 PFU, while two- and three-week-old mice were used for ip inoculations of 100 PFU. Following ip inoculation either with the parent virus or with IC37, the mortalities were 100% for two-week-old mice, and 50% for three-week-old mice. See FIG. 6, parts A and B. Intracerebral inoculations with the parent virus or with IC37 resulted in mortalities of 100% for three- and five-week old mice. See FIG. 6, parts C and D. All mice survived inoculation of IC47 without any signs of illness.

EXAMPLE 3

Neutralizing Antibody Production and Viremia in Mice Infected with Parent or IC47 Viruses For these studies, three-week-old Swiss ICR mice were inoculated ip with 100 PFU of the parent virus or IC47 virus. Serum samples were collected at various time points and neutralizing antibody and viremia were measured as follows. To determine neutralizing antibody titers, 10–160 fold dilutions of serum samples were prepared and incubated overnight at 4° C. with 50 PFU of the parent virus. The virus titer of the reaction was determined by a plaque assay in which a monolayer of BHK-21 cells in 35 or 60mm dishes was inoculated with virus, washed with PBS and overlaid with 1% agarose containing 2% fetal calf serum in MEM. After two-three days, cells were stained with neutral red or crystal violet to visualize plaques. A 70% reduction in plaques indicated the presence of a neutralizing antibody titer.

Figure 7:
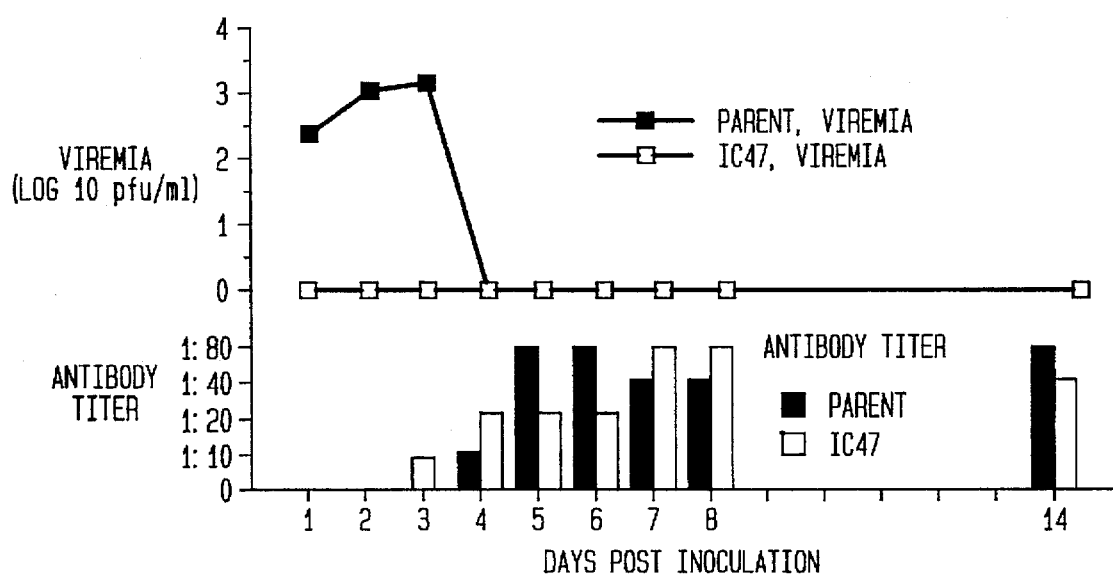
FIG. 7 shows the presence of viremia and neutralizing antibody production in three-week-old mice inoculated either with parent JEV or with recombinant mutant JEV (IC47).
Figure 6A:
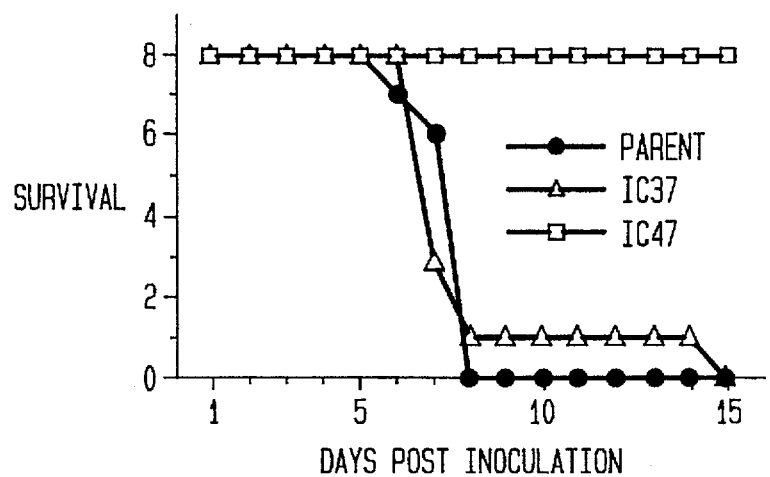
FIG. 6 shows the survival rates of Swiss ICR outbred mice challenged with parent JEV, recombinant wild-type JEV (IC37) or recombinant mutant JEV (IC47). Part A: two-week-old mice inoculated by the intraperitoneal (ip) route. Part B: three-week-old mice inoculated by the ip route. Part C: three-week-old mice inoculated by the intracerebral (ic) route. Part D: five-week-old mice inoculated by the ic route with parent and IC47 viruses.
Figure 6B:
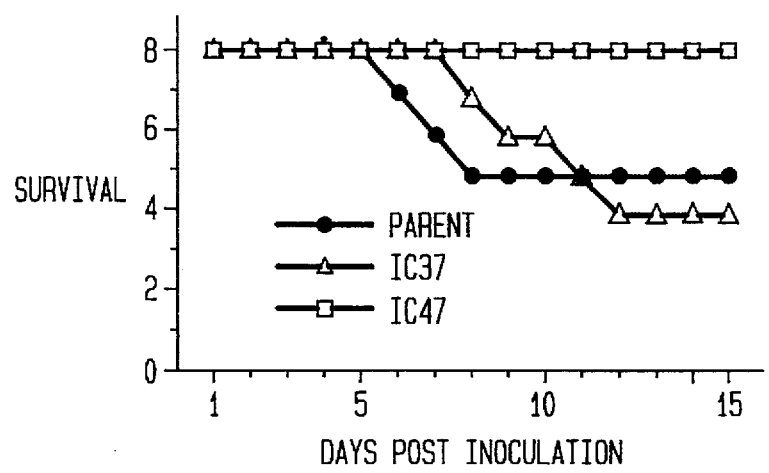
Figure 6C:
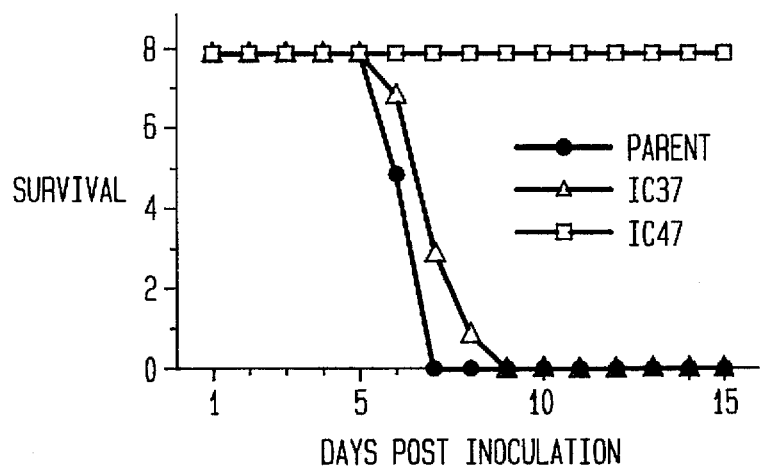
Figure 6D:
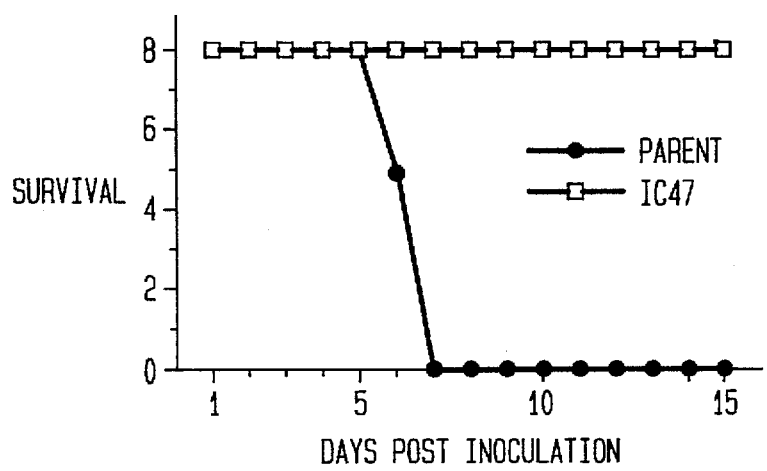

Neutralizing antibodies were detected three to four days following inoculation in both treatment groups. See FIG. 7. Differences in neutralizing antibody production were relatively minor.

To measure the presence of viremia, serum samples were added to BHK-21 monolayers, and virus titer was determined by the plaque assay. Viremia was detected in mice inoculated with the parent virus with maximum titers of about $10^3$ PFU/ml on day three. See FIG. 7. When antibody titers began to rise, detectable viremia began to decrease; no virus was detected at day four. Although viremia was not detectable in sera from mice inoculated with IC47, virus probably replicated in these mice, since the mice mounted an antibody response that was similar to the antibody response to the parent virus.

EXAMPLE 4

Virus Growth in Brain

To examine the growth of virus in brain tissue, mice were infected with 100 PFU of parent JEV, recombinant wild-type JEV IC37 or IC47, using ic or ip administration. Brains were harvested at various times following inoculation, and tissue samples were homogenized in 50% FCS in MEM (4:1; w/v). The virus titer of brain homogenate was determined by plaque assay, as described above.

Figure 8A:
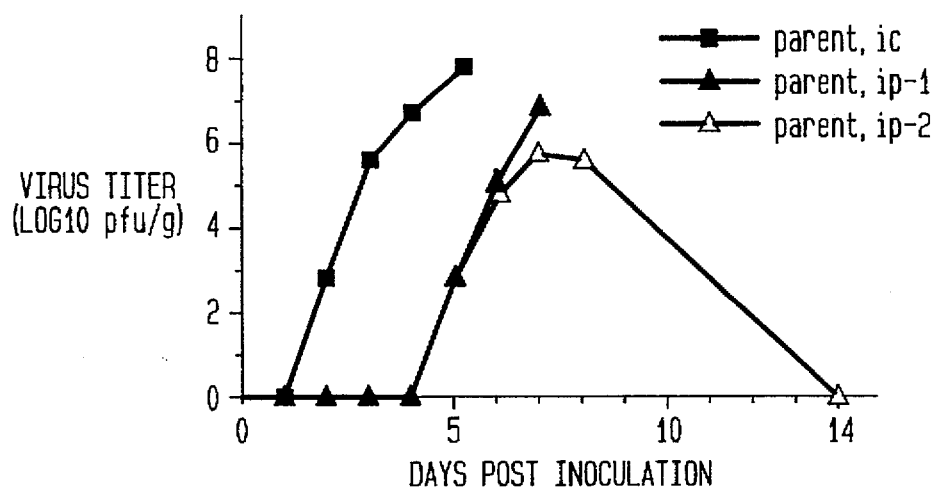
FIG. 8 shows the titer of either parent JEV or recombinant mutant JEV (IC47) in the brains of ICR mice. Part A: virus titers of mice inoculated with parent virus by the ip route were determined from moribund mice (closed triangle, ip-1) and from healthy mice (open triangle, ip-2). Part B: inoculation with recombinant mutant virus.
Figure 8B:
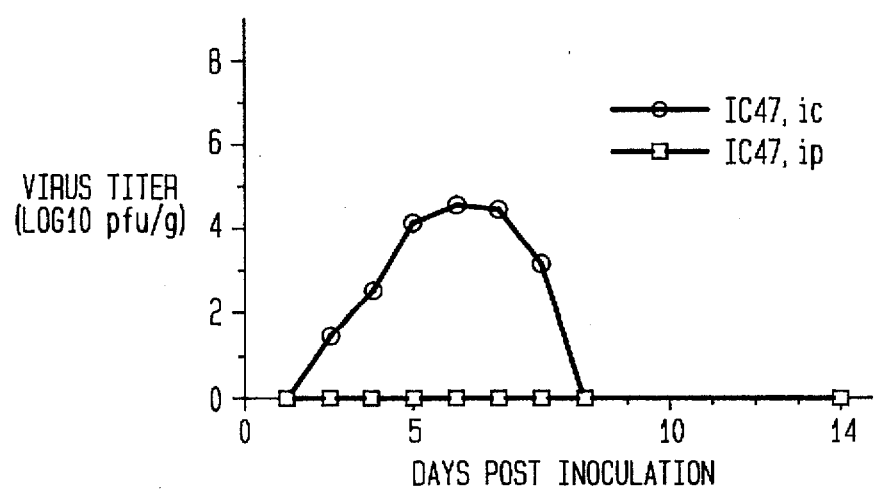

When the parent virus was inoculated by the ic route, virus titers in the brain increased immediately, reaching levels of more than $10^7$ PFU/gm on day five. See FIG. 8, part A. By day seven, all mice had died from the infection. Following ip inoculation with the parent, virus appeared in the brain at day five. Mice that had brain virus titers greater than $10^7$ PFU/gm became paralyzed and died (FIG. 8, part A, closed triangles), while mice in groups with brain virus titers less than $10^6$ PFU/g remained healthy (open triangles). Virus was cleared by day 14 from the brains of the surviving mice.

In mice inoculated ic with IC47, the virus started to grow immediately in brain tissue, but IC47 accumulated in the brain more slowly, compared with the parent virus, and IC47 attained lower titers than those observed for the parent. See FIG. 8, part B. The maximum brain titer was approximately $10^{4.7}$ PFU/gm at day five. IC47 was cleared from brain by day eight. Virus was not detected in brain tissue of mice that had been inoculated with IC47 by ip administration.

EXAMPLE 5

Immunization-Challenge study

To determine whether IC47 could be used to provide protective immunity against the parent virus, three groups of eight mice were inoculated with 100 PFU of IC47. Two-week-old mice were inoculated ip, while three-week-old mice were inoculated either by the ip route or by the ic route. Two weeks following inoculation with IC47, mice were challenged with 100 PFU of parent virus by the ic route.

Figure 9:
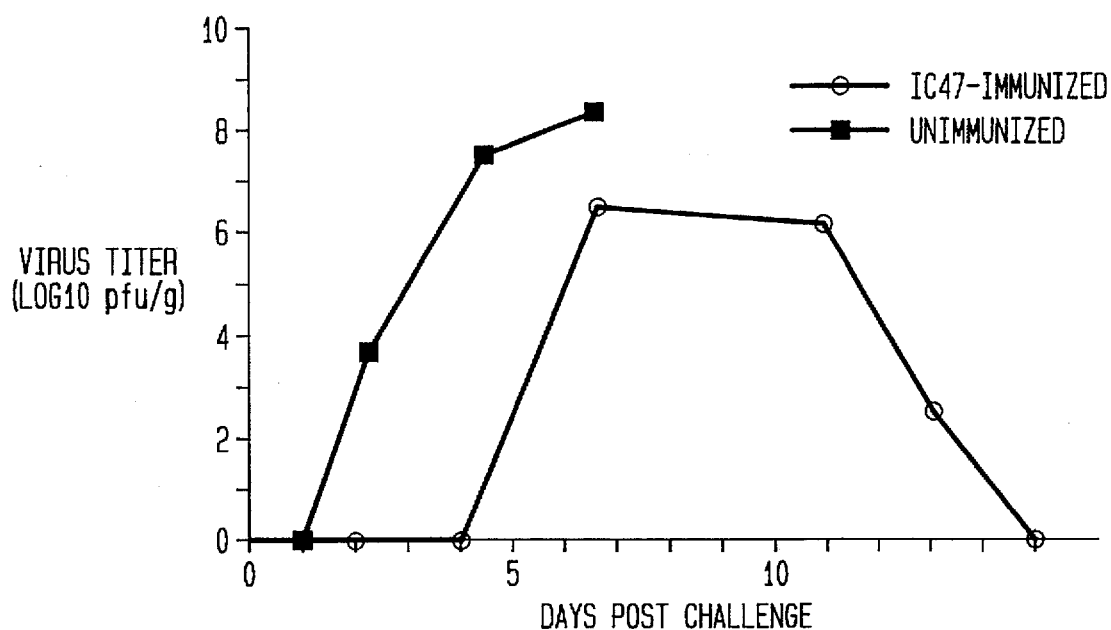
FIG. 9 shows virus titer in brains of IC47-immunized mice that had been challenged with the parent virus by the ic route.

Although all non-immunized mice died by day seven, all mice treated with IC47 survived the challenge without any sign of illness. The maximum virus titer of the challenged mice was below $10^7$PFU/gm brain tissue, which was ten times lower than the titer observed in brains of non-immunized mice. See FIG. 9. The parent virus was cleared from brain tissue by day 14.

EXAMPLE 6

Computer Simulation of Envelop Protein Structure

Several simulation programs are available for prediction of protein structure based on the amino acid sequence data. These programs were used to compare the predicted envelop protein structure of recombinant wild-type IC37 and recombinant attenuated IC47, which has the $^{138}$Lys mutation. The Chou-Fasman program and the Garnier-Osguthorpe-Robinson program were used to predict secondary structure, including alpha helices, beta sheets, and turns. Chou et al., *Adv. Enz. Relat. Areas Mol. Biol.* 47: 45 (1978); Garnier et al., *J. Mol. Biol.* 120: 97 (1978). Other programs were used to predict additional parameters such as hydrophilicity, surface probability, flexibility, and antigenicity. Hopp et al., *Proc. Nat'l Acad. Sci. U.S.A.* 78: 3824 (1981); Emini et al., *J. Virology* 55: 836 (1985); Jameson BA et al., *Computer Applications in the Biosciences* 4: 181 (1988).

There was no significant difference in the results of the simulation for hydrophilicity, surface probability, flexibility and antigenicity. Both Chou-Fasman and Garnier-Osguthorpe-Robinson programs, however, predicted differences in the secondary structure of the two viruses. According to the Chou-Fasman program, there are differences in turns, alpha helices and beta sheets. The Garnier-Osguthorpe-Robinson program predicted a difference in turns between the envelop proteins of the two viruses. Therefore, it is possible that the $^{138}$Lys mutation changes the conformation of the envelop protein leading to attenuated phenotype of IC47.

EXAMPLE 7

Characterization of Recombinant Viruses Having $^{138}$Asp and $^{138}$Arg Mutations in the Envelop Protein Site-directed mutagenesis was used to produce recombinant viruses having the following mutations at position 138 of the envelop protein: Arg (AGA) ["$^{138}$Arg"], Arg (AGG)

and Asp (GAC) ["$^{138}$Asp"]. DNA sequence analysis was used to verify the nucleotide substitutions.

Figure 10:
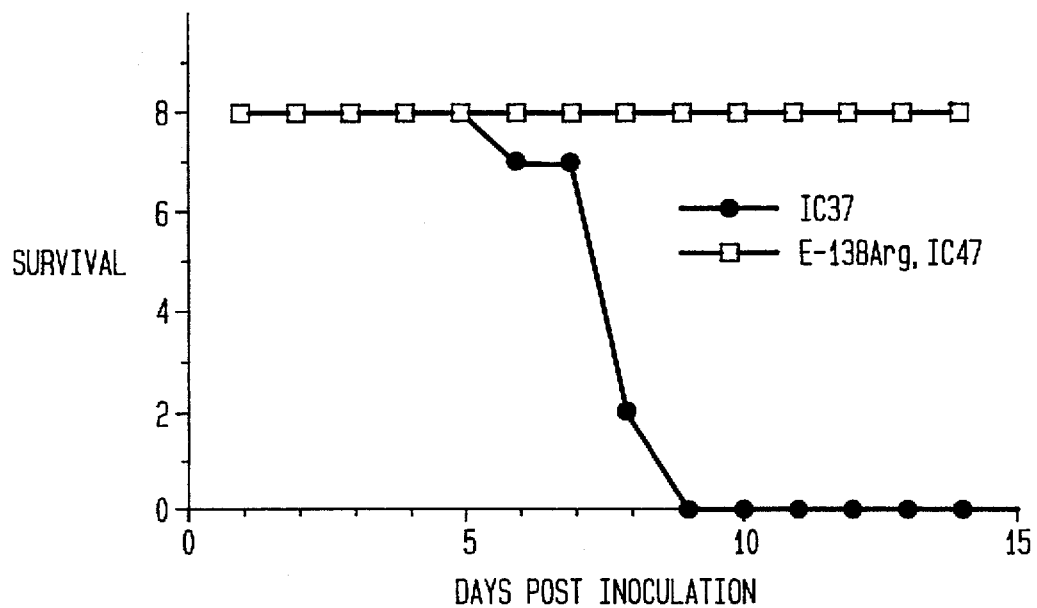
FIG. 10 shows the induction of neurovirulence by recombinant wild-type IC37 virus, IC47 virus or $^{138}$Arg virus in three-week old mice.

The ability of recombinant mutant viruses to induce neurovirulence was examined by inoculating three-week old mice by the ic route with 100 PFU of recombinant wild-type IC37, IC47, $^{138}$Arg or $^{138}$Asp. All of the mice that had been inoculated with IC37 or $^{138}$Asp died. In contrast, all mice that had been inoculated with IC47 or $^{138}$Arg survived without any sign of illness. See FIG. 10.

Figure 11:
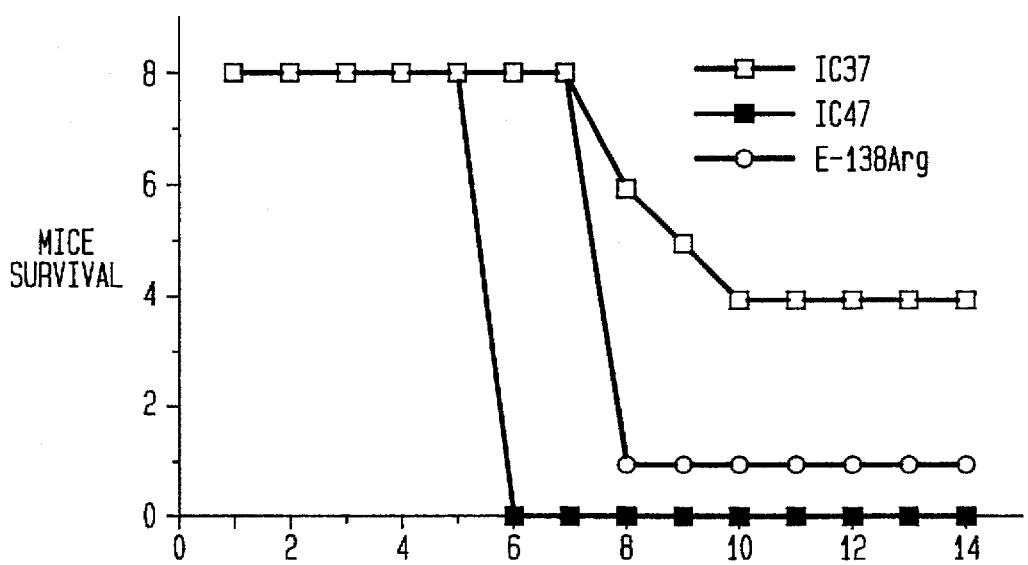
FIG. 11 shows the induction of neurovirulence by recombinant wild-type IC37 virus, IC47 virus or $^{138}$Arg virus in five-day old mice.

Neurovirulence analysis also was performed with groups of eight five-day old mice. In these studies, all mice died by day six following inoculation with IC37. See FIG. 11. IC47 and $^{138}$Arg also were neurovirulent in these new-born mice.

These studies showed that IC47 and $^{138}$Arg induced neurovirulence in five-day old mice, but not in three-week old mice. This pattern of susceptibility is similar to that observed for yellow fever 17D, which is an established, attenuated vaccine used to protect humans against yellow fever virus.

To determine whether $^{138}$Arg can induce neutralizing antibody production, three-week old ICR mice were inoculated with 100 PFU of the virus. Neutralizing antibody titers were measured in blood samples obtained seven and fourteen days following inoculation. A titer of 1:80 was observed in both serum samples. These results indicate that $^{138}$Arg is as immunogenic as IC47.

In a challenge study, three-week old mice were inoculated with 100 PFU of $^{138}$Arg. Two weeks later, the mice were injected ic with 100 PFU of IC37. Although all non-immunized mice died by day seven, all mice immunized with $^{138}$Arg survived the lethal challenge without any sign of illness. Accordingly, $^{138}$Arg and IC47 appear to provide protective immunity to a similar extent.

IC47 and $^{138}$Arg were passaged in mouse brains to determine the genetic stability of the mutations that provide the attenuated phenotype. In these studies, both viruses were administered ic to three-week old mice, and the mice were sacrificed on the fourth day following injection. Brain homogenates were prepared as described above, and were designated as P1. Portions of the P1 homogenates were used to inoculate a second group of mice, and brain homogenates from these mice were designated P2. This cycle was continued for ten blind passages.

One hundred PFU of IC47 virus or $^{138}$Arg virus isolated from P10 homogenates were administered ic to three-week old mice to determine neurovirulence. The results of these studies showed that the attenuated phenotype was stable after ten passages. DNA sequence analyses of viruses from P10 homogenates verified the stability of the IC47 and $^{138}$Arg mutations. Revertants were not observed after the ten passages.

In summary, the $^{138}$Arg virus is highly attenuated, highly immunogenic, induces protective immunity, is genetically stable and contains a double mutation in the codon encoding amino acid 138 of the envelop protein. The neurovirulence characteristics of the $^{138}$Arg virus are similar to those of the yellow fever vaccine, 17D. The attenuated phenotype of both IC47 and $^{138}$Arg viruses is stable after ten blind passages through mouse brain. Since the $^{138}$Arg virus has a double mutation and IC47 has a single mutation, the $^{138}$Arg virus may prove to be more genetically stable than IC47 over a long period of time.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

All publications and patent applications mentioned in this specification are indicative of the level of skill of those in the art to which the invention pertains. All publications and patent applications are herein incorporated by reference to the same extent as if each individual publication or patent application were specifically and individually indicated to be incorporated by reference in its entirety.

What is claimed is:

1. An isolated, mutant Japanese encephalitis virus (JEV) that possesses a single mutation characterized in that an acidic amino acid selected from the group consisting of glutamic acid and aspartic acid at position 138 of the envelope protein is replaced with a basic amino acid selected from the group consisting of lysine and arginine.

2. The mutant JEV of claim 1, wherein said wild-type JEV is JEV strain JaOArS982, and wherein said acidic amino acid is glutamic acid.

3. The mutant JEV of claim 2, wherein said basic amino acid is lysine.

4. The mutant JEV of claim 3, wherein said mutant JEV is IC47 (ATCC No. VR 2412).

5. The mutant JEV of claim 2, wherein said basic amino acid is arginine.

6. A pharmaceutical composition for providing protection from virulent Japanese encephalitis virus, wherein said pharmaceutical composition comprises (a) the mutant JEV of claim 1, and (b) a pharmaceutically acceptable vehicle.

7. The pharmaceutical composition of claim 6, wherein said basic amino acid is lysine.

8. The pharmaceutical composition of claim 7, wherein said mutant JEV is IC47 (ATCC No. VR 2412).

9. The pharmaceutical composition of claim 6, wherein said basic amino acid is arginine.

* * * * *